(12) United States Patent
Estell

(10) Patent No.: US 7,033,817 B2
(45) Date of Patent: Apr. 25, 2006

(54) PROTEASES FROM GRAM POSITIVE ORGANISMS

(75) Inventor: David A. Estell, San Mateo, CA (US)

(73) Assignee: Genencor International, Inc., Palo Alto, CA (US)

( * ) Notice: Subject to any disclaimer, the term of this patent is extended or adjusted under 35 U.S.C. 154(b) by 488 days.

(21) Appl. No.: 10/177,412

(22) Filed: Jun. 21, 2002

(65) Prior Publication Data

US 2006/0035367 A1    Feb. 16, 2006

Related U.S. Application Data

(62) Division of application No. 09/555,000, filed on May 23, 2000, now Pat. No. 6,489,108.

(30) Foreign Application Priority Data

Dec. 30, 1997  (GB)  .................................. 9727470

(51) Int. Cl.
*C12N 15/00* (2006.01)
*C12N 9/54* (2006.01)
*C12N 15/57* (2006.01)
*C12N 15/75* (2006.01)
*C11D 3/386* (2006.01)

(52) U.S. Cl. .............. 435/252.31; 435/221; 435/320.1; 435/471; 510/300; 536/23.2

(58) Field of Classification Search ................ 435/222, 435/471, 69.1, 252.31, 320.1; 426/63; 510/300
See application file for complete search history.

(56) References Cited

U.S. PATENT DOCUMENTS

| | | | |
|---|---|---|---|
| 3,817,837 A | 6/1974 | Rubenstein et al. ..... 195/103.5 |
| 3,840,466 A | 10/1974 | Gray ........................... 510/306 |
| 3,850,752 A | 11/1974 | Schuurs et al. .......... 195/103.5 |
| 3,939,350 A | 2/1976 | Kronick et al. ............. 250/365 |
| 3,996,345 A | 12/1976 | Ullman et al. ................. 424/12 |
| 4,261,868 A | 4/1981 | Hora et al. ................... 252/529 |
| 4,275,149 A | 6/1981 | Litman et al. .................. 435/7 |
| 4,277,437 A | 7/1981 | Maggio ........................ 422/61 |
| 4,366,241 A | 12/1982 | Tom et al. ...................... 435/7 |
| 4,404,128 A | 9/1983 | Anderson .................... 252/548 |
| 4,533,359 A | 8/1985 | Kondo et al. ................... 8/128 |
| 4,816,567 A | 3/1989 | Cabilly et al. ............... 530/387 |
| 5,147,642 A | 9/1992 | Lotz et al. ................ 424/94.61 |
| 5,204,015 A | 4/1993 | Caldwell et al. ......... 252/174.12 |
| 5,264,366 A * | 11/1993 | Ferrari et al. ........... 435/252.31 |
| 5,314,692 A | 5/1994 | Haarasilta et al. .......... 424/94.2 |
| 5,411,873 A * | 5/1995 | Adams et al. .............. 435/69.1 |
| 5,585,253 A | 12/1996 | Doi et al. ................. 435/172.3 |
| 5,589,373 A * | 12/1996 | Weiner et al. ............... 435/220 |
| 5,612,055 A | 3/1997 | Bedford et al. .............. 424/442 |
| 5,677,272 A * | 10/1997 | Ghosh et al. ................ 510/306 |
| 6,300,117 B1 * | 10/2001 | Estell .......................... 435/221 |
| 6,465,186 B1 * | 10/2002 | Estell ............................. 435/6 |
| 6,489,108 B1 * | 12/2002 | Estell ............................. 435/6 |
| 6,521,440 B1 * | 2/2003 | Estell ....................... 435/252.3 |
| 6,528,255 B1 * | 3/2003 | Estell ............................. 435/6 |
| 6,599,731 B1 * | 7/2003 | Estell ....................... 435/252.1 |
| 6,794,179 B1 * | 9/2004 | Estell .................... 435/252.31 |
| 6,833,265 B1 * | 12/2004 | Estell .................... 435/252.31 |

FOREIGN PATENT DOCUMENTS

| | | |
|---|---|---|
| EP | 0 134 267 B1 | 8/1989 |
| EP | 0 369 817 * | 5/1990 |
| EP | 0 344 250 | 5/1993 |
| EP | 0 590 746 A1 | 4/1994 |
| GB | 2 031 948 | 4/1980 |
| WO | WO 88/06623 | 9/1988 |
| WO | WO 89/10976 | 11/1989 |
| WO | WO 95/10615 | 4/1995 |
| WO | WO 95/14099 | 5/1995 |
| WO | WO 99/33959 A2 * | 7/1999 |
| WO | WO 99/33960 A2 * | 7/1999 |
| WO | WO 99/34002 A2 * | 7/1999 |
| WO | WO99/34003 A2 * | 7/1999 |

OTHER PUBLICATIONS

EMBL/GenBank Databases Accession no Z99116, Sequence reference BSUB0013,Nov. 20, 1997,Kunst F et al:'The complete genome sequence of the Gram-positive bacterium Bacillus subtilis ', XP002105783.

EMBL/GenBank Databases accession no F69964, Dec. 5, 1997, Kunst K et al:'Amino acid degradation homolog ygjN', XP002105785, * the whole document*.

(Continued)

Primary Examiner—Nashaat T. Nashed
Assistant Examiner—William W. Moore
(74) Attorney, Agent, or Firm—Genencor Internattional, Inc.

(57) ABSTRACT

The present invention relates to the identification of a novel metalloproteases in gram positive microorganisms. The present invention provides the nucleic acid and amino acid sequences for the metalloprotease. The present invention also provides host cells having a mutation or deletion of part or all of the gene encoding the metalloprotease. The present invention provides host cells which further comprises a nucleic acid encoding desired heterologous proteins such as enzymes. The present invention also provides cleaning compositions, animal feeds and compositions used to treat a textile that include the metalloprotease of the present invention.

12 Claims, 10 Drawing Sheets

OTHER PUBLICATIONS

*Database Swiss-Prot [Online]*, Feb 1, 1995, Glaser P et al : "Bacillus subti lis genome project", Database accession No. P39635, XP002252294, *abstract*.

Calogero S et al, "ROCR, A Novel Regulatory Protein Controlling Atginine Utilization In Bacillus Subtilis, Belongs To The Ntrc/Nifa Family Of Transcriptional Activators", *Journal of Bacteriology*, US, vol. 176(5), Mar. 1, 1994, pp. 1234-1241, XP000670046.

Bauza T et al., "Determination of biogenic amines and their precursor amino acids in wines of the Vallee du Rhone by high-performance liquid chromatography with precolumn derivatization and fluorimetric detection", *Journal of Chromatography A, Elsevier Science*, NL, vol. 707, No. 2, Jul. 21, 1995, pp. 373-379, XP004038826.

*Kunst, F. et al., "The complete genome sequence of the Gram-positive bacterium *Bacillus subtilis*," Nature, vol. 390, pp. 249-264, Nov. 20, 1997—See IDS submitted Jun. 21, 2002.

Document No. 216034, date Apr. 1982, country RD.

*Ausubel et al., Current Protocols in Molecular Biology, John Wiley & Sons, Inc., vol. 1, Ch. 2 and 9, 1987.

*Bakhiet et al., "Studies on Transfection and Transformation of Protoplasts of *Bacillus Larvae, Bacillus subtilis,* and *Bacillus popilliae*," Applied and Environmental Microbiology, vol. 49, No. 3, pp. 577-581, Mar., 1985.

*Fischer et al., "Introduction of plasmid pC194 into *Bacillus thuringiensis* by Protoplast transformation and plasmid transfer," Arch. of Microbiol., vol. 139, pp. 213-217, 1984.

*Grunstein et al., "Colony hybridization: A method for the isolation of cloned DNAs that contain a specific gene," Proc. Nat. Acad. Sci. USA, vol. 72, No. 10, pp. 3961-3965, Oct., 1975.

*Haima, Peter et al., "Novel plasmid marker rescue transformation system for molecular cloning in *Bacillus subtilis* enabling direct selection of recombinants," Mol. Gen. Genet., vol. 223, pp. 185-191, 1990.

*Holubova et al., "Transfer of Liposome-Encapsulated Plasmid DNA to *Bacillus subtilis* Protoplasts and Calcium-Treated *Escherichia coli* Cells," Folia Microbiol., vol. 30, pp. 97-100, 1985.

*Kroll et al., "A Multifunctional Prokaryotic Protein Expression System: Overproduction, Affinity Purification, and Selective Detection," DNA and Cell Biology, vol. 12, No. 5, pp. 441-453, 1993.

*Kunst, F. et al., "The complete genome sequence of the Gram-positive bacterium *Bacillus subtilis*," Nature, vol. 390, pp. 249-264, Nov. 20, 1997.

*Maddox et al., "Elevated Serum Levels in Human Pregnancy of a Molecule Immunochemically Similar to Eosinophil Granule Major Basic Protein," J. Exp. Med., vol. 158, pp. 1211-1226, Oct., 1983.

*Mann et al., "Transformation of *Bacillus spp.*: an Examination of the Transformation of *Bacillus* Protoplasts by Plasmids pUB110 and pHV33," Current Microbiology, vol. 13, pp. 191-195, 1986.

*Margot, Philippe et al., "The *wprA* gene of *Bacillus subtilis* 168, expressed during exponential growth, encodes a cell-wall-associated protease," Microbiology, vol. 142, pp. 3437-3444, 1996.

*Margot, Philippe et al., "The gene of the N-acetylglucominidase, a *Bacillus subtilis* 168 cell wall hydrolase not involved in vegetative cell autolysis," Mol. Microbiology, vol. 12, pp. 535-545, 1994.

*McDonald et al., "Plasmid Transformation of *Bacillus sphaericus* 1593," Journal of General Microbiology, vol. 130, pp. 203-208, 1984.

*Murray et al., "Codon usage in plant genes," Nucleic Acids Research, vol. 17, No. 2, pp. 477-498, 1989.

*Porath, Jerker "Immobilized Metal Ion Affinity Chromatography," Protein Expression and Purification, vol. 3, pp. 263-281, 1992.

*Sadaie et al., "Nucleotide sequence and analysis of the phoB-rmE-groESL region of the *Bacillus subtilis* chromosome," Microbiology, vol. 143, pp. 1861-1866, 1997.

*Smith, Michael et al., "Protoplast Transformation in Coryneform Bacteria and Introduction of an α-Amylase Gene from *Bacillus amyloliquefaciens* into *Brevibacterium lactofermentum*," Applied and Environmental Microbiology, vol. 51, No. 3, pp. 634-639, Mar., 1986.

*Vorobjeva, I.P. et al., "Transformation of *Bacillus Megaterium* Protoplasts by Plasmid DNA," FEMS Microbiology Letters 7, pp. 261-263, 1980.

*Ward, Michael et al., "Proteinases, In Microbiol Enzymes and Biotechnology," (W. M. Fogerty, ed), Applied Science, London, pp. 251-317, 1983.

*Weinrauch et al., "Plasmid Marker Rescue Transformation Proceeds by Breakage-Reunion in *Bacillus subtilis*," Journal of Bacteriology, vol. 169, No. 3, pp. 1205-1211, Mar., 1987.

* cited by examiner

```
ATCAAGTCATTTCTTTCCCGTCATATAAACTGCTCAAATGAACCGCTTTTGTCAAACATT
----+----+----+----+----+----+----+----+----+----+----+----+  60
TAGTTCAGTAAAGAAAGGGCAGTATATTTGACGAGTTTACTTGGCGAAAACAGTTTGTAA

TCTGTATAATAGACGAGAAATCAGTTTATTTTTTCAGTATAGAAGCATTTTTATTCATAGG
----+----+----+----+----+----+----+----+----+----+----+----+ 120
AGACATATTATCTGCTCTTTAGTCAAATAAAAAGTCATATCTTCGTAAAAATAAGTATCC

AGGGGCGGAATCAATGAATTGGCAGACGAAGGACGAATTGCTGGCACTTTTAACTTCTCT
----+----+----+----+----+----+----+----+----+----+----+----+ 180
TCCCCGCCTTAGTTACTTAACCGTCTGCTTCCTGCTTAACGACCGTGAAAATTGAAGAGA
                 Met Asn Trp Gln Thr Lys Asp Glu Leu Leu Ala Leu Leu Thr Ser Leu
                                            yqjN TGTGCAATACGAAAGCATCACCGGTTCAAAGGGCGAGGTAGCGCTTGCAGAGTATCTTTA
----+----+----+----+----+----+----+----+----+----+----+----+ 240
ACACGTTATGCTTTCGTAGTGGCCAAGTTTCCCGCTCCATCGCGAACGTCTCATAGAAAT
Val Gln Tyr Glu Ser Ile Thr Gly Ser Lys Gly Glu Val Ala Leu Ala Glu Tyr Leu Tyr
                              yqjN
```

FIG._1A

```
TTTTATTTTGAAGGACAAGCCCTATTTTCAAAAGCACCCTGATGATGTAACACCCTCATCC
----+----+----+----+----+----+----+----+----+----+----+----+ 300
AAAATAAAACTTCCTGTTCGGGATAAAAGTTTTCGTGGGACTACTACATTGTGGAGTAGG

Phe Ile Leu Lys Asp Lys Pro Tyr Phe Gln Lys His Pro Asp Asp Val Thr Pro His Pro
                                          ─────────────────────────────────────────
                                                         yqjN GATGGACGGATGGCAGATCTTTTCTTACGGGCTCTAGTCAAAAAGAAGAATGTCAAAAAGAC
----+----+----+----+----+----+----+----+----+----+----+----+ 360
CTACCTGCTACCGTCTAGAAAAGAATGCCCGAGATCAGTTTTTCTTCTTACAGTTTTTCTG Met Asp Asp Gly Arg Ser Phe Leu Thr Ala Leu Val Lys Lys Asn Val Lys Lys Thr
─────────────────────────────────────────────────────────────────────────
                              yqjN AGTCCTTCTGCTGAGTCATTTTGATGTCGTTGACATAGAAGATTACGGGCGAATTTAAACA
----+----+----+----+----+----+----+----+----+----+----+----+ 420
TCAGGAAGACGACTCAGTAAAACTACAGCAACTGTATCTTCTAATGCCCGCTTAAATTTGT Val Leu Leu Leu Ser His Phe Asp Val Val Asp Ile Glu Asp Tyr Gly Glu Phe Lys His
─────────────────────────────────────────────────────────────────────────────
                              yqjN TATGGCTTGCAAGCCTGCTGAGCTTTTGAGCTCCTTTTTAGAGAAAAAGAGCTGCTCCC
----+----+----+----+----+----+----+----+----+----+----+----+ 480
ATACCGAACGTTCGGACGACTCGAAAACTCGAGGAAAAATCTCTTTTTCTCGACGAGGG Met Ala Cys Lys Pro Ala Glu Leu Leu Ser Ser Phe Leu Glu Lys Lys Glu Leu Leu Pro
─────────────────────────────────────────────────────────────────────────────
                              yqjN
```

FIG._1B

```
GGAACGTGTGAGAAGAGATGCCGAAAGCGGAGACTGGCTGTTCGGAAGAGGACGATGGA
     ------+---------+---------+---------+---------+---------+ 540
CCTTGCACACTCTTCTCTACGGCTTCGCCTCTGACCGACAAGCCTTCTCCCTGCTACCT

Glu Arg Val Arg Arg Asp Ala Glu Ser Gly Asp Trp Leu Phe Gly Arg Gly Thr Met Asp
                                         yqjN
                                         ───

TATGAAAAGCGGGGCTTTGTATTCAACTGTCGATGCTGGAGAGGCAATGAACGGGCATTT
     ------+---------+---------+---------+---------+---------+ 600
ATACTTTTCGCCCCGAAACATAAGTTGACAGCTACGACCTCTCCGTTACTTGCCCGTAAA

Met Lys Ala Gly Leu Cys Ile Gln Leu Ser Met Leu Glu Arg Ala Met Asn Gly His Phe
                                         yqjN
                                         ───

TGAGGGCAATCTGCTGTTGATAACGGTTCCGGACGAGGAAGTGAATTCAAGAGGCATGAT
     ------+---------+---------+---------+---------+---------+ 660
ACTCCCGTTAGACGACAACTATTGCCAAGGCCTGCTCCTTCACTTAAGTTCTCCGTACTA

Glu Gly Asn Leu Leu Ile Thr Val Pro Asp Glu Glu Val Asn Ser Arg Gly Met Ile
                                         yqjN
                                         ───

TGAAGCGGGTTCCTGCATTGAAGGAGATGGAGAAAAAGCATGATATCACATTAACCGCTTG
     ------+---------+---------+---------+---------+---------+ 720
ACTTCGCCCAAGGACGTAACTTCCTCTACCTCTTTTTCGTACTATAGTGTAATTGGCGAAC

Glu Ala Val Pro Ala Leu Lys Glu Met Glu Lys Lys His Asp Ile Thr Leu Thr Ala Cys
                                         yqjN
                                         ───
```

FIG._1C

```
CCTGAATGCCGAACCGATGTTTGAAAAATTTCCCGGGATCAGCAGCAATATTTTATAC
                                                          ——+—— 780
GGACTTACGGCTTGGCTACAAACTTTTTAAAGGGCCCTAGTCGTCGTTATAAAATATG

Leu Asn Ala Glu Pro Met Phe Glu Lys Phe Pro Gly Asp Gln Gln Tyr Phe Tyr Thr
                                         yqjN AGGAAGCATTGGCAAGGTGCTTGCGGGTTTTTTCTGCAAGGGGATTGAGACACATGTTGG
                                                              ——+—— 840
TCCTTCGTAACCGTTCCACGAACGCCCAAAAAAGACGTTCCCCTAACTCTGTGTACAACC Gly Ser Ile Gly Lys Val Leu Ala Gly Phe Phe Cys Lys Gly Ile Glu Thr His Val Gly
                                         yqjN AGAGCCGTTTTCAGGTCTAAACGCAAATTTAATGGTATCTGAGATTAACCGTTTGCTTGA
                                                              ——+—— 900
TCTCGGCAAAAGTCCAGATTTGCGTTTAAATTACCATAGACTCTAATTGGCAAACGAACT Glu Pro Phe Ser Gly Leu Asn Ala Asn Leu Met Val Ser Glu Ile Asn Arg Leu Leu Glu
                                         yqjN ACTGAATGCTGATTATTGCGAAAAGGTTGATGGCGAGGTCACTCCGCCGCCGGTAAACTT
                                                              ——+—— 960
TGACTTACGACTAATAACGCTTTTCCAACTACCGCTCCAGTGAGGCGGCGGCCATTTGAA Leu Asn Ala Asp Tyr Cys Glu Lys Val Asp Gly Glu Val Thr Pro Pro Val Asn Leu
                                         yqjN
```

*FIG. _ 1D*

```
AATGCAAAAGGACTTGAAAGAGGCATATATTCAGTCCAGACACCGCATACAGCCGTCACATT
----+----+----+----+----+----+----+----+----+----+----+----+    1020
TTACGTTTTCCTGAACTTTCTCCGTATAAGTCAGGTCTGTGGCGTATGTCGGCAGTGTAA
 Met Gln Lys Asp Leu Lys Glu Ala Tyr Ser Val Gln Thr Pro His Thr Ala Val Thr Leu
                                              yqjN ATTTAATGTGCTGTCAATGAAACGCTCAGCTAGTGAGCTGCATCAGATGCTGCTTAAAAC
----+----+----+----+----+----+----+----+----+----+----+----+    1080
TAAATTACACGACAGTTACTTTGCGAGTCGATCACTCGACGTAGTCTACGACGAATTTTG
 Phe Asn Val Leu Ser Met Lys Arg Ser Ala Ser Glu Leu His Gln Met Leu Leu Lys Thr
                                              yqjN AGCAGAACAGGGCGGGCGGAGGAAATCATGTCGAACGTTCGGAAGAAAAACACAGGATTTTCA
----+----+----+----+----+----+----+----+----+----+----+----+    1140
TCGTCTTGTCCGCCCGCCCTCCTTTAGTACAGCTTGCAAGCCTTCTTTTTGTGTCCTAAAAGT
 Ala Glu Gln Ala Ala Glu Glu Ile Met Ser Asn Val Arg Lys Lys Thr Gln Asp Phe Gln
                                              yqjN ACAATTTGAGCCATTTCAGCCGGATTGAGCGGGACGTCACTGTTTTGACATTTGATGAGCT
----+----+----+----+----+----+----+----+----+----+----+----+    1200
TGTTAAACTCGGTAAAGTCGGCTAACTCGCCCTGCAGTGACAAAACTGTAAACTACTCGA
 Gln Phe Glu Pro Ile Gln Pro Ile Glu Arg Asp Val Thr Val Leu Thr Phe Asp Glu Leu
                                              yqjN
```

FIG._1E

```
GGTCTCGCGGTGCAAAAAGCGTGCGGGGGATCTCGGAAACAGAGCGGGGCTCTAAATTATGC
        ----+----|----+----|----+----|----+----|----+----|----+----|    1260
CCAGAGCGCACGTTTTTCGCACGCCCCTAGAGCCTTTGTCTCGCCCGAGATTTAATACG

Val Ser Arg Ala Lys Lys Arg Ala Gly Ile Ser Glu Arg Ala Leu Asn Tyr Ala
                                        ─────────────────────────────
                                                    yqjN CTTTGCTAACAGGGGGGGAGCTTGGAGACAGGGATTTTTCGACGAAAATTGTTTCTGAGCT
        ----+----|----+----|----+----|----+----|----+----|----+----|    1320
GAAACGATTGTCCCCCCCTCGAACCTCTGTCCCTAAAAAGCTGCTTTTAACAAAGACTCGA Phe Ala Asn Arg Gly Glu Leu Gly Asp Arg Asp Phe Ser Thr Lys Ile Val Ser Glu Leu
─────────────────────────────────────────────────────────────────────
                                yqjN TGCTTCGCTTTGTAAGGAGGATGCGCCGCTCATCGTTCTGTTTTATAGTCCGCCGCTTTA
        ----+----|----+----|----+----|----+----|----+----|----+----|    1380
ACGAAGCGAAACATTCCTCCTACGCGGCGAGTAGCAAGACAAAATATCAGGCGGCGAAAT Ala Ser Leu Cys Lys Glu Asp Ala Pro Leu Ile Val Leu Phe Tyr Ser Pro Pro Leu Tyr
─────────────────────────────────────────────────────────────────────
                                yqjN TCCAGCTGTTTCTTCAAAGGATGATCAATTGATCAGAAATACAGCAGATCAGATAAAGCA
        ----+----|----+----|----+----|----+----|----+----|----+----|    1440
AGGTCGACAAAGAAGTTTCCTACTAGTTAACTAGTCTTTATGTCGTCTAGTCTATTTCGT Pro Ala Val Ser Ser Lys Asp Asp Gln Leu Ile Arg Asn Thr Ala Asp Gln Ile Lys His
─────────────────────────────────────────────────────────────────────
                                yqjN
```

FIG._1F

```
TTATGCGGCTGAGGCGATACGGGCATTGCATTACGGGAGGTTCAGTACTTCCCGGACTTTC
-----+---------+---------+---------+---------+---------+      1500
AATACGCCGACTCGCTATGCCCGTAACGTAATGCCCTCCAAGTCATGAAGGGCCTGAAAG

Tyr Ala Ala Glu Arg Tyr Gly Ile Ala Leu Arg Glu Val Gln Tyr Phe Pro Gly Leu Ser
                                            yqjN GGACTTGAGTTATCTTCAGCTGGAAAAAACAGGAGGTTGATGCATACACAAGCAATATGCC
-----+---------+---------+---------+---------+---------+      1560
CCTGAACTCAATAGAAGTCGACCTTTTGTCCTCCAACTACGTATGTGTTCGTTATACGG Asp Leu Ser Tyr Leu Gln Leu Glu Lys Gln Glu Val Asp Ala Tyr Thr Ser Asn Met Pro
                                            yqjN GCTCTTTAACAGAGGGTATTCATTGCCAAGCGGTAAAAATCAGGCTTTATATGTCCCAGT
-----+---------+---------+---------+---------+---------+      1620
CGAGAAATTGTCTCCCATAAGTAACGGTTCGCCATTTTTAGTCCGAAATATACAGGGTCA Leu Phe Asn Arg Gly Tyr Ser Leu Pro Ser Gly Lys Asn Gln Ala Leu Tyr Val Pro Val
                                            yqjN TTTAAAATGTCGGTCCGGCTGGTAAAGACCCGCATAAATGGACGGAAAGATTGTATATGCC
-----+---------+---------+---------+---------+---------+      1680
AAATTTACAGCCAGGCCGACCATTTCTGGGCGTATTACCTGCCTTTCTAACATATACGG Leu Asn Val Gly Pro Ala Gly Lys Asp Pro His Lys Trp Thr Glu Arg Leu Tyr Met Pro
                                            yqjN
```

FIG._1G

```
TTATTCCTTTGAAGTGCTTCCCGATTTGCTTTCATTTACGATCTCCGCGCTATTAAAGCA
------+---------+---------+---------+---------+---------+  1740
AATAAGGAAACTTCACGAAGGGCTAAACGAAAGTAAATGCTAGAGGCGGATAATTTCGT
 Tyr Ser Phe Glu Val Leu Pro Asp Leu Ser Phe Thr  Ile Ser  Ala Leu Leu Lys Gln
                                              ─────────────────────────────
                                                         yqjN ATCAGAATCTGCCGGCCAGCTGCTGCGGGAAAATAAAAACAGAAGGCACTGTGCCTTC
------+---------+---------+---------+---------+---------+  1800
TAGTCTTAGACGGCCGGTCGACGACGCCCTTTTATTTTTTGTCTTCCGTGACACGGAAG
 Ser Glu Ser  Ala Gly Gln Leu Leu Arg Glu Lys
─────────────────────────────
           yqjN TGTTTTTGTCCTTACATCTAAGAATGTCTCTCTAAGGCGGCACCGGCAAACTGTTCTTTG
------+---------+---------+---------+---------+---------+  1860
ACAAAAACAGGAATGTAGATTCTTACAGAGAGATTCCGCCGTGGCCGTTTGACAAGAAAC ATTTCTGCGCTCCGTTTAGCTGTTTCTTCAATACAGTGAA
------+---------+---------+---------+-->  1900
TAAAGACGCGAGGCAAATCGACAAAGAAGTTATGTCACTT
```

*FIG._1H*

```
DE   SUCCINYL-DIAMINOPIMELATE DESUCCINYLASE (EC 3.5.1.18) (SDAP).
GN   DAPE OR MSGB.
OS   ESCHERICHIA COLI.
CC   -!- CATALYTIC ACTIVITY: N-SUCCINYL-LL-2,6-DIAMINOHEPTANEDIOATE + H(2)O
CC       = SUCCINATE + LL-2,6-DIAMINOHEPTANEDIOATE.
CC   -!- DAPE/MSGB IS A MULTICOPY SUPPRESSOR OF A TEMPERATURE-SENSITIVE
CC       ALLELE OF THE HEAT SHOCK GENE GRPE.
CC   -!- COFACTOR: COBALT OR ZINC.
CC   -!- PATHWAY: FIFTH STEP IN THE BIOSYNTHESIS OF DIAMINOPIMELATE AND
CC       LYSINE FROM ASPARTATE SEMIALDEHYDE.
CC   -!- SIMILARITY: BELONGS TO PEPTIDASE FAMILY M20B; ALSO KNOWN AS THE
CC       ARGE/DAPE/ACY1/CPG2/YSCS FAMILY.
DR   EMBL; S41760; G253061; -.
DR   EMBL; X57403; G41234; -.
DR   PIR; A42958; A42958.
DR   PIR; A42959; A42959.
DR   ECOGENE; EG10208; DAPE.
DR   PROSITE; PS00758; ARGE_DAPE_CPG2_1.
DR   PROSITE; PS00759; ARGE_DAPE_CPG2_2.
KW   DIAMINOPIMELATE BIOSYNTHESIS; LYSINE BIOSYNTHESIS; HYDROLASE; COBALT;
KW   ZINC.

[NOTE: generally conserved residues are D99, D132, E133, E134, H193,
and E352 using dape_ecoli numbering. - DAE]

YqjN: 547 AA - 2474 kb - Function unknown dape_ecoli.pep
BSUPEP:YQJN

YqjN 547 AA - 2474 kb

SCORES    Init1:    68  Initn:    68  Opt:   147  z-score: 171.5  E():  0.00038
Smith-Waterman score: 147;    27.9% identity in 136 aa overlap
```

FIG._2A

```
dape_ecoli.p  AFAGHTDVPPGDADRWINPFEPTIRDGMLFGRGAADMKGSLAAMVVAAERFVAQHPNH
                70        80        90       100       110       120
              ||||:||||::|:::|||:::|||:::
YQJN          CKPAELLSSFLEKKELLPERVRRDAESGDWLFGRGTMDMKAGLCIQLSMLER---AMNGHF
              100       110       120       130       140       150 dape_ecoli.p  TGRLAFLITSDEEASAHNGTVKVVEALMARNERLDY----CLVGEPSSIEVVGDVVK---
              130       140       150       160       170
              |:::||:||:|||::|||:
YQJN          EGNLLLITVPDEEVNSR-GMIEAVPALKEMEKKHDITLTACLNAEPMFEKFPGDQQQYFY
              160       170       180       190       200       210 dape_ecoli.p  NGRRGSLTCNLTIHGVQGHVAYPHLADNPVHRAAPFLNELVAIEWDQGNEFFPATSMQIA
              180       190       200       210       220       230
              :|:::::|||||:::|::|::|
YQJN          TGSIGKVLAGFFCKGIETHVGEPFSGLN-ANLMVSEINRLLELNADYCEKVDGEVTPPPV
              220       230       240       250       260       270 dape_ecoli.p  NIQAGTGSNNVIPGELFVQFNFRFSTELTDEMIKAQVLALLEKHQLRYTVDWWLSGQPFL
              240       250       260       270       280       290
YQJN          NLMQKDLKEAYSVQTPHTAVTLFNVLSMKRSASELHQMLLKTAEQAAEEIMSNVRKKTQD
              280       290       300       310       320       330
```

PROTEASES FROM GRAM POSITIVE ORGANISMS

This is a Divisional of U.S. patent application Ser. No. 09/555,000, filed on May 23, 2002, now U.S. Pat. No. 6,489,108, which claims priority under 35 USC §371, to PCT/US98/26971, filed Dec. 17, 1998, and GB 9727470, filed Dec. 30, 1997.

FIELD OF THE INVENTION

The present invention relates to metalloproteases derived from gram positive microorganisms. The present invention provides nucleic acid and amino acid sequences of a metalloproteases identified in *Bacillus*. The present invention also provides methods for the production of the metalloprotease in host cells as well as the production of heterologous proteins in a host cell having a mutation or deletion of part or all of the metalloprotease of the present invention.

BACKGROUND OF THE INVENTION

Gram positive microorganisms, such as members of the group *Bacillus*, have been used for large-scale industrial fermentation due, in part, to their ability to secrete their fermentation products into the culture media. In gram positive bacteria, secreted proteins are exported across a cell membrane and a cell wall, and then are subsequently released into the external media usually maintaining their native conformation.

Various gram positive microorganisms are known to secrete extracellular and/or intracellular proteases at some stage in their life cycles. Some of these proteases are produced in large quantities for industrial purposes. However, a negative aspect of the presence of proteases in gram positive organisms is their contribution to the overall degradation of secreted heterologous or foreign proteins.

The classification of proteases found in microorganisms is based on their catalytic mechanism which results in four groups: serine proteases, metalloproteases, cysteine proteases, and aspartic proteases. These categories can be distinguished by their sensitivity to various inhibitors. For example, serine proteases are inhibited by phenylmethylsulfonylfluoride (PMSF) and diisopropylfluorophosphate (DIFP); metalloproteases by chelating agents; cysteine proteases by iodoacetamide and heavy metals and aspartic proteases by pepstatin. Further, in general, serine proteases have alkaline pH optima, metalloproteases are optimally active around neutrality, and cysteine and aspartic proteases have acidic pH optima (*Biotechnology Handbooks, Bacillus*. Vol. 2, edited by Harwood, 1989, Plenum Press, New York).

Metallo-proteases form the most diverse of the catalytic types of proteases. Family M20b is also known as the glutamate carboxypeptidase family and includes bacterial enzymes such as the glutamate carboxypeptidase from *Pseudomonas* spp., succinyldiaminopimelate desuccinylase (DAPE) from *E. coli* and acetylornithine deacetylase (ARGE) also from *E. coli* (Methods in Enzymology, vol. 248, Academic Press, Inc. 1994). Preferred metal ions for the enzymes of the M20b family include zinc and/or cobalt.

SUMMARY OF THE INVENTION

The present invention relates to the discovery of a heretofore unknown metalloprotease (MP) found in gram positive microorganisms, uses of the MP in industrial applications, and advantageous strain improvements based on genetically engineering such microorganisms to delete, underexpress or overexpress that MP. The present invention is based upon the discovery that MP has overall amino acid relatedness to succinyldiaminopimelate desuccinylase (DAPE) from *E. coli*.

Applicant's discovery, in addition to providing a new and useful protease and methods of detecting DNA encoding other such proteases in a gram positive microorganism, provides several advantages which may facilitate optimization and/or modification of strains of gram positive microorganisms, such as *Bacillus*, for expression of desired, e.g. heterologous, proteins. Such optimizations, as described below in detail, allow the construction of strains having decreased proteolytic degradation of desired expression products.

Due to the relatedness of MP to DAPE and ARGE, zinc metalloendopeptidases which have been shown to degrade small peptides of less than 7 kd such as glucagon and insulin, it can be concluded that MP is also an endopeptidase and would be expected to behave similarly to DAPE and ARGE.

The present invention encompasses the naturally occurring MP encoded by nucleic acid found in a *Bacillus* species as well as the nucleic acid and amino acid molecules having the sequences disclosed in SEQ ID NOS: 1 and 2. In one embodiment, the gram positive microorganism is a *Bacillus*. In a further embodiment, the *Bacillus* is preferably selected from the group consisting of *Bacillus subtilis, Bacillus stearothermophilus, Bacillus licheniformis* and *Bacillus amyloliquefaciens*. The invention further provides for a metalloprotease that has at least 80%, preferably at least 90%, most preferably 95% homology with the amino acid sequence of SEQ ID NO: 2. The invention also provides for a nucleic acid which encodes a metalloprotease that has at least 80%, preferably at least 90%, most preferably 95% homology with the nucleotide sequence shown in SEQ ID NO:1.

In a preferred embodiment, the present invention encompasses the naturally occurring MP nucleic acid molecule having the sequence found in *Bacillus subtilis* I-168 strain (*Bacillus* Genetic Stock Center, accession number 1A1, Columbus, Ohio) in the region of about 2474 kb from the point of origin. In another preferred embodiment, the *Bacillus subtilis* MP nucleic acid and amino acid molecules have the sequences as shown in FIGS. 1A–1D (SEQ ID NOS:1 and 2).

The present invention provides isolated polynucleotide and amino acid sequences for *Bacillus subtilis* MP in FIGS. 1A–1D (SEQ ID NOS:1 and 2). Due to the degeneracy of the genetic code, the present invention encompasses any nucleic acid sequence that encodes the *Bacillus subtilis* MP amino acid sequence. The present invention provides expression vectors and host cells comprising a nucleic acid encoding a gram positive MP. The present invention also provides methods of making the gram positive MP.

The present invention encompasses novel amino acid variations of gram positive MP amino acid sequences disclosed herein that have proteolytic activity. Naturally occurring gram positive MP as well as proteolytically active amino acid variations or derivatives thereof, have application in the textile industry, in cleaning compositions and in animal feed.

The present invention also encompasses amino acid variations or derivatives of gram positive MP that do not have the characteristic proteolytic activity as long as the nucleic acid sequences encoding such variations or derivatives would have sufficient 5' and 3' coding regions to be capable of being integrated into a gram positive organism genome.

Such variants would have applications in gram positive expression systems where it is desirable to delete, mutate, alter or otherwise incapacitate the naturally occurring metalloprotease in order to diminish or delete its proteolytic activity. Such an expression system would have the advantage of allowing for greater yields of recombinant heterologous proteins or polypeptides.

The present invention provides methods for detecting gram positive microorganism homologues of *B. subtilis* MP that comprises hybridizing part or all of the nucleic acid encoding *B. subtilis* MP with nucleic acid derived from gram positive organisms, either of genomic or cDNA origin. Accordingly, the present invention provides a method for detecting a gram positive microorganism MP, comprising the steps of hybridizing gram positive microorganism nucleic acid under low stringency conditions to a probe, wherein the probe comprises part or all of the nucleic acid sequence shown in FIGS. 1A–1D (SEQ ID NO:1); and isolating the gram positive nucleic acid which hybridizes to said probe.

The production of desired heterologous proteins or polypeptides in gram positive microorganisms may be hindered by the presence of one or more proteases which degrade the produced heterologous protein or polypeptide. One advantage of the present invention is that it provides methods and expression systems which can be used to prevent that degradation, thereby enhancing yields of the desired heterologous protein or polypeptide.

Accordingly, the present invention provides a gram positive microorganism that can be used as a host cell having a mutation or deletion of part or all of the gene encoding MP, which results in the inactivation of the MP proteolytic activity, either alone or in combination with mutations in other proteases, such as apr, npr, epr, mpr, bpf or isp, or other proteases known to those of skill in the art. In one embodiment of the present invention, the gram positive microorganism is a member of the genus *Bacillus*. In a preferred embodiment, the *Bacillus* is selected from the group consisting of *B. subtilis, B. licheniformis, B. lentus, B. brevis, B. stearothermophilus, B. alkalophilus, B. amyloliquefaciens, B. coagulans, B. circulans, B. lautus* and *B. thuringiensis*. In a further preferred embodiment, the *Bacillus* is *Bacillus subtilis*.

In another aspect, the gram positive host cell having one or more metalloprotease deletions or mutations is further genetically engineered to produce a desired protein. In one embodiment of the present invention, the desired protein is heterologous to the gram positive host cell. In another embodiment, the desired protein is homologous to the host cell.

In another embodiment, a host cell is engineered to produce MP. The gram positive microorganism may be normally sporulating or non-sporulating. In a preferred embodiment, the gram positive host cell is a *Bacillus*. In another embodiment, the *Bacillus* is selected from the group consisting of *B. subtilis, B. licheniformis, B. lentus, B. brevis, B. stearothermophilus, B. alkalophilus, B. amyloliquefaciens, B. coagulans, B. circulans, B. lautus* and *B. thuringiensis*. In a further preferred embodiment, the *Bacillus* host cell is *Bacillus subtilis*.

In a further aspect of the present invention, gram positive MP is produced on an industrial fermentation scale in a microbial host expression system. In another aspect, isolated and purified recombinant MP is used in compositions intended for use in the textile industry, in cleaning compositions, such as detergents, and in animal feeds. Accordingly, the present invention provides a cleaning composition, animal feed and a composition for the treatment of a textile comprising MP. The metalloprotease, MP, may be used alone or in combination with other enzymes and/or mediators or enhancers.

As noted, the present invention provides a cleaning composition comprising a metalloprotease, MP, comprising the amino acid sequence shown in SEQ ID NO:2. Also provided are cleaning compositions comprising a metalloprotease having at least 80%, preferably 90%, more preferably 95% homology with the amino acid sequence shown in SEQ ID NO:2 or comprising a metalloprotease encoded by a gene that hybridizes with the nucleic acid shown in SEQ ID NO:1.

Further there is provided an animal feed comprising a metalloprotease, MP, comprising the amino acid sequence shown in SEQ ID NO:2. Also provided are animal feeds comprising a metalloprotease having at least 80%, preferably 90%, more preferably 95% homology with the amino acid sequence shown in SEQ ID NO:2 or comprising a metalloprotease encoded by a gene that hybridizes with the nucleic acid shown in SEQ ID NO:1.

Also provided is a composition for the treatment of a textile comprising a metalloprotease, MP, comprising the amino acid sequence shown in SEQ ID NO:2. Also provided are compositions for the treatment of a textile comprising a metalloprotease having at least 80%, preferably 90%, more preferably 95% homology with the amino acid sequence shown in SEQ ID NO:2 or comprising a metalloprotease encoded by a gene that hybridizes with the nucleic acid shown in SEQ ID NO:1.

BRIEF DESCRIPTION OF THE DRAWINGS

FIGS. 1A–1H show the DNA and amino acid sequence for *Bacillus subtilis* MP (YqjN) (SEQ ID NOS: 1 and 2).

FIG. 2 shows an amino acid alignment of *Escherichia coli* succinyl-diaminopimelate desuccinylase and *Bacillus subtilis* MP (YqjN).

DETAILED DESCRIPTION OF THE PREFERRED EMBODIMENTS

Definitions

As used herein, the genus *Bacillus* includes all members known to those of skill in the art, including but not limited to *B. subtilis, B. licheniformis, B. lentus, B. brevis, B. stearothermophilus, B. alkalophilus, B. amyloliquefaciens, B. coagulans, B. circulans, B. lautus* and *B. thuringiensis*.

The present invention relates to a newly characterized metalloprotease (MP) from gram positive organisms. In a preferred embodiment, the gram positive organisms is a *Bacillus*. In another preferred embodiment, the *Bacillus* is selected from the group consisting of *B. subtilis, B. licheniformis, B. lentus, B. brevis, B. stearothermophilus, B. alkalophilus, B. amyloliquefaciens, B. coagulans, B. circulans, B. lautus* and *B. thuringiensis*.

In another preferred embodiment, the gram positive organism is *Bacillus subtilis* and MP has the amino acid sequence encoded by the nucleic acid molecule having the sequence that occurs around 2474 kilobases from the point of origin of *Bacillus subtilis* I-168.

In another preferred embodiment, MP has the nucleic acid and amino acid sequence as shown in FIGS. 1A–1D (SEQ ID NOS: 1 and 2). The present invention encompasses the use of amino acid variations of the amino acid sequences disclosed in FIGS. 1A–1D (SEQ ID NO: 2) that have proteolytic activity. Such proteolytic amino acid variants can be used in the textile industry, animal feed and cleaning compositions. The present invention also encompasses the use of *B. subtilis* amino acid variations or derivatives that are not proteolytically active. DNA encoding such variants can be used in methods designed to delete or mutate the naturally occurring host cell MP.

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand. As used herein "amino acid" refers to peptide or protein sequences or portions thereof. A "polynucleotide homologue" as used herein refers to a gram positive microorganism polynucleotide that has at least 80%, preferably at least 90% and more preferably at least 95% identity to *B. subtilis* MP, or which is capable of hybridizing to *B. subtilis* MP under conditions of high stringency and which encodes an amino acid sequence having metalloprotease activity.

The terms "isolated" or "purified" as used herein refer to a nucleic acid or amino acid that is removed from at least one component with which it is naturally associated.

As used herein, the term "heterologous protein" refers to a protein or polypeptide that does not naturally occur in the chosen gram positive host cell. Examples of heterologous proteins include enzymes such as hydrolases including proteases, cellulases, carbohydrases such as amylases, and lipases; isomerases such as racemases, epimerases, tautomerases, or mutases; oxidases, reductases, transferases, kinases and phophatases. The heterologous gene may encode therapeutically significant proteins or peptides, such as growth factors, cytokines, ligands, receptors and inhibitors, as well as vaccines and antibodies. The gene may encode commercially important industrial proteins or peptides, such as proteases, carbohydrases such as amylases and glucoamylases, cellulases, oxidases and lipases. The gene of interest may be a naturally occurring gene, a mutated gene or a synthetic gene.

The term "homologous protein" refers to a protein or polypeptide native or naturally occurring in the chosengram positive host cell. The invention includes host cells producing the homologous protein via recombinant DNA technology. The present invention encompasses a gram positive host cell having a deletion or interruption of the nucleic acid encoding the naturally occurring homologous protein, such as a protease, and having nucleic acid encoding the homologous protein re-introduced in a recombinant form. In another embodiment, the host cell produces the homologous protein.

As used herein, the term "overexpressing" when referring to the production of a protein in a host cell means that the protein is produced in greater amounts than in its naturally occurring environment.

As used herein, the phrase "proteolytic activity" refers to a protein that is able to hydrolyze a peptide bond. Enzymes having proteolytic activity are described in Enzyme Nomenclature, 1992, edited Webb Academic Press, Inc.

The unexpected discovery of the metalloprotease MP found in translated uncharacterised *B. subtilis* genomic sequences provides a basis for producing host cells, expression methods and systems which can be used to prevent the degradation of recombinantly produced heterologous proteins.

Accordingly, in a preferred embodiment, the host cell is a gram positive host cell that has a deletion or mutation in the naturally occurring nucleic acid encoding MP said mutation resulting in deletion or inactivation of the production by the host cell of the MP proteolytic gene product. The host cell may additionally be genetically engineered to produced a desired protein or polypeptide.

It may also be desired to genetically engineer host cells of any type to produce a gram positive metalloprotease. Such host cells are used in large scale fermentation to produce large quantities of the metalloprotease which may be isolated or purified and used in cleaning products, such as detergents.

I. Metalloprotease Sequences

The present invention encompasses the use of MP polynucleotide homologues encoding gram positive microorganism metalloproteases MP which have at least 80%, preferably at least 90%, more preferably at least 95% identity to *B. subtilis* MP as long as the homologue encodes a protein that has proteolytic activity. A preferred MP polynucleotide homologue has 96% homology to *B. subtilis* MP.

Gram positive polynucleotide homologues of *B. subtilis* MP may be obtained by standard procedures known in the art from, for example, cloned DNA (e.g., a DNA "library"), genomic DNA libraries, by chemical synthesis once identified, by cDNA cloning, or by the cloning of genomic DNA, or fragments thereof, purified from a desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. 1, 11.) A preferred source is from genomic DNA.

As will be understood by those of skill in the art, the polynucleotide sequence and amino acid sequence disclosed in FIGS. 1A–1D may reflect inadvertent errors inherent to nucleic acid sequencing technology. The present invention encompasses the naturally occurring nucleic acid molecule having the nucleic acid sequence obtained from the genomic sequence of *Bacillus* species.

Nucleic acid encoding *Bacillus subtilis* MP starts around 2474 kilobases counting from the point of origin in the *Bacillus subtilis* strain I-168 (Anagnostopala, 1961, *J. Bacteriol.*, 81:741–746 or *Bacillus* Genomic Stock Center, accession 1A1, Columbus, Ohio). The *Bacillus subtilis* point of origin has been described in Ogasawara, N. (1995, Microbiology 141:Pt.2 257–59). *Bacillus subtilis* MP has a length of 547 amino acids. Based upon the location of the DNA encoding *Bacillus subtilis* MP, naturally occurring *B. subtilis* MP can be obtained by methods known to those of skill in the art including PCR technology.

Oligonucleotide sequences or primers of about 10–30 nucleotides in length can be designed from the polynucleotide sequence disclosed in FIGS. 1A–1D and used in PCR technology to isolate the naturally occurring sequence from *B. subtilis* genomic sequences.

Another general strategy for the "cloning" of *B. subtilis* genomic DNA pieces for sequencing uses inverse PCR. A known region is scanned for a set of appropriate restriction enzyme cleavage sites and inverse PCR is performed with a set of DNA primers determined from the outermost DNA sequence. The DNA fragments from the inverse PCR are directly used as template in the sequencing reaction. The newly derived sequences can be used to design new oligonucleotides. These new oligonucleotides are used to amplify DNA fragments with genomic DNA as template. The sequence determination on both strands of a DNA region is finished by applying a primer walking strategy on the genomic PCR fragments. The benefit of multiple starting points in the primer walking results from the series of inverse PCR fragments with different sizes of new "cloned"

DNA pieces. From the most external DNA sequence, a new round of inverse PCR is started. The whole inverse PCR strategy is based on the sequential use of conventional taq polymerase and the use of long range inverse PCR in those cases in which the taq polymerase failed to amplify DNA fragments. Nucleic acid sequencing is performed using standard technology. One method for nucleic acid sequencing involves the use of a Perkin-Elmer Applied Biosystems 373 DNA sequencer (Perkin-Elmer, Foster City, Calif.) according to manufacturer's instructions.

Nucleic acid sequences derived from genomic DNA may contain regulatory regions in addition to coding regions. Whatever the source, the isolated MP gene should be molecularly cloned into a suitable vector for propagation of the gene.

In molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the MP may be accomplished in a number of ways. For example, a *B. subtilis* MP gene of the present invention or its specific RNA, or a fragment thereof, such as a probe or primer, may be isolated and labeled and then used in hybridization assays to detect a gram positive MP gene. (Benton, W. and Davis, R., 1977, *Science* 196:180; Grunstein, M. and Hogness, D., 1975, *Proc. Natl. Acad. Sci. USA* 72:3961). Those DNA fragments sharing substantial sequence similarity to the probe will hybridize under stringent conditions.

Accordingly, the present invention provides a method for the detection of gram positive MP polynucleotide homologues which comprises hybridizing part or all of a nucleic acid sequence of *B. subtilis* MP with gram positive microorganism nucleic acid of either genomic or cDNA origin.

Also included within the scope of the present invention is the use of gram positive microorganism polynucleotide sequences that are capable of hybridizing to the nucleotide sequence of *B. subtilis* MP under conditions of intermediate to maximal stringency. Hybridization conditions are based on the melting temperature (Tm) of the nucleic acid binding complex, as taught in Berger and Kimmel (1987, *Guide to Molecular Cloning Techniques, Methods in Enzymology*, Vol. 152, Academic Press, San Diego, Calif.) incorporated herein by reference, and confer a defined "stringency" as explained below.

"Maximum stringency" typically occurs at about Tm −5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologues.

The term "hybridization" as used herein shall include "the process by which a strand of nucleic acid joins with a complementary strand through base pairing" (Coombs, J., (1994), *Dictionary of Biotechnology*, Stockton Press, New York, N.Y.).

The process of amplification as carried out in polymerase chain reaction (PCR) technologies is described in Dieffenbach, C W and G S Dveksler, (*PCR Primer, a Laboratory Manual*, Cold Spring Harbor Press, Plainview, N.Y., 1995). A nucleic acid sequence of at least about 10 nucleotides and as many as about 60 nucleotides from *B. subtilis* MP, preferably about 12 to 30 nucleotides, and more preferably about 20–25 nucleotides can be used as a probe or PCR primer.

The *B. subtilis* MP amino acid sequences (shown in FIGS. 1A–1D) were identified via a BLAST search (Altschul, Stephen, Basic local alignment search tool, *J. Mol. Biol.*, 215:403–410) of *Bacillus subtilis* genomic nucleic acid sequences. *B. subtilis* MP (YqjN) was identified by its overall nucleic acid identity to the metalloprotease, succinyl-diaminopimelate desuccinylase from *Escherichia coli*.

II. Expression Systems

The present invention provides host cells, expression methods and systems for the enhanced production and secretion of desired heterologous or homologous proteins in gram positive microorganisms. In one embodiment, a host cell is genetically engineered to have a deletion or mutation in the gene encoding a gram positive MP such that the respective activity is deleted. In another embodiment of the present invention, a gram positive microorganism is genetically engineered to produce and/or overproduce a metalloprotease of the present invention.

Inactivation of a Gram Positive Metalloprotease in a Host Cell

Producing an expression host cell incapable of producing the naturally occurring metalloprotease necessitates the replacement and/or inactivation of the naturally occurring gene in the genome of the host cell. In a preferred embodiment, the mutation is a non-reverting mutation.

One method for mutating a nucleic acid encoding a gram positive metalloprotease is to clone the nucleic acid or part thereof, modify the nucleic acid by site directed mutagenesis and reintroduce the mutated nucleic acid into the cell on a plasmid. By homologous recombination, the mutated gene can be introduced into the chromosome. In the parent host cell, the result is that the naturally occurring nucleic acid and the mutated nucleic acid are located in tandem on the chromosome. After a second recombination, the modified sequence is left in the chromosome having thereby effectively introduced the mutation into the chromosomal gene for progeny of the parent host cell.

Another method for inactivating the metalloprotease proteolytic activity is through deleting the chromosomal gene copy. In a preferred embodiment, the entire gene is deleted, the deletion occurring in such as way as to make reversion impossible. In another preferred embodiment, a partial deletion is produced, provided that the nucleic acid sequence left in the chromosome is too short for homologous recombination with a plasmid encoding the metalloprotease gene. In another preferred embodiment, nucleic acid encoding the catalytic amino acid residues are deleted.

Deletion of the naturally occurring gram positive microorganism metalloprotease can be carried out as follows. A metalloprotease gene including its 5' and 3' regions is isolated and inserted into a cloning vector. The coding region of the metalloprotease gene is deleted from the vector in vitro, leaving behind a sufficient amount of the 5' and 3' flanking sequences to provide for homologous recombination with the naturally occurring gene in the parent host cell. The vector is then transformed into the gram positive host cell. The vector integrates into the chromosome via homologous recombination in the flanking regions. This method leads to a gram positive strain in which the protease gene has been deleted.

The vector used in an integration method is preferably a plasmid. A selectable marker may be included to allow for ease of identification of desired recombinant microorganisms. Additionally, as will be appreciated by one of skill in the art, the vector is preferably one which can be selectively integrated into the chromosome. This can be achieved by introducing an inducible origin of replication, for example, a temperature sensitive origin into the plasmid. By growing the transformants at a temperature to which the origin of replication is sensitive, the replication function of the plasmid is inactivated, thereby providing a means for selection of chromosomal integrants. Integrants may be selected for growth at high temperatures in the presence of the selectable marker, such as an antibiotic. Integration mechanisms are described in WO 88/06623.

Integration by the Campbell-type mechanism can take place in the 5' flanking region of the protease gene, resulting in a protease positive strain carrying the entire plasmid vector in the chromosome in the metalloprotease locus. Since illegitimate recombination will give different results, it will be necessary to determine whether the complete gene has been deleted, such as through nucleic acid sequencing or restriction maps.

Another method of inactivating the naturally occurring metalloprotease gene is to mutagenize the chromosomal gene copy by transforming a gram positive microorganism with oligonucleotides which are mutagenic. Alternatively, the chromosomal metalloprotease gene can be replaced with a mutant gene by homologous recombination.

The present invention encompasses host cells having additional protease deletions or mutations, such as deletion of or mutation(s) in the genes encoding apr, npr, epr, mpr and others known to those of skill in the art.

One assay for the detection of mutants involves growing the Bacillus host cell on medium containing a protease substrate and measuring the appearance or lack thereof, of a zone of clearing or halo around the colonies. Host cells which have an inactive protease will exhibit little or no halo around the colonies.

III. Production of Metalloprotease

For production of metalloprotease in a host cell, an expression vector comprising at least one copy of nucleic acid encoding a gram positive microorganism MP, and preferably comprising multiple copies, is transformed into the host cell under conditions suitable for expression of the metalloprotease. In accordance with the present invention, polynucleotides which encode a gram positive microorganism MP, or fragments thereof, or fusion proteins or polynucleotide homologue sequences that encode amino acid variants of B. subtilis MP, may be used to generate recombinant DNA molecules that direct their expression in host cells. In a preferred embodiment, the gram positive host cell belongs to the genus Bacillus. In a further preferred embodiment, the gram positive host cell is B. subtilis.

As will be understood by those of skill in the art, it may be advantageous to produce polynucleotide sequences possessing non-naturally occurring codons. Codons preferred by a particular gram positive host cell (Murray, E. et al., (1989), Nuc. Acids Res., 17:477–508) can be selected, for example, to increase the rate of expression or to produce recombinant RNA transcripts having desirable properties, such as a longer half-life, than transcripts produced from a naturally occurring sequence.

Altered MP polynucleotide sequences which may be used in accordance with the invention include deletions, insertions or substitutions of different nucleotide residues resulting in a polynucleotide that encodes the same or a functionally equivalent MP homologue, respectively. As used herein a "deletion" is defined as a change in the nucleotide sequence of the MP resulting in the absence of one or more amino acid residues.

As used herein, an "insertion" or "addition" is that change in the nucleotide sequence which results in the addition of one or more amino acid residues as compared to the naturally occurring MP.

As used herein, "substitution" results from the replacement of one or more nucleotides or amino acids by different nucleotides or amino acids, respectively. The change(s) in the nucleotides(s) can either result in a change in the amino acid sequence or not.

The encoded protein may also show deletions, insertions or substitutions of amino acid residues which produce a silent change and result in a functionally equivalent MP variant. Deliberate amino acid substitutions may be made on the basis of similarity in polarity, charge, solubility, hydrophobicity, hydrophilicity, and/or the amphipathic nature of the residues as long as the variant retains its proteolytic ability. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine, phenylalanine, and tyrosine.

The MP polynucleotides of the present invention may be engineered in order to modify the cloning, processing and/or expression of the gene product. For example, mutations may be introduced using techniques which are well known in the art, i.e., site-directed mutagenesis to insert new restriction sites, to alter glycosylation patterns or to change codon preference, for example.

In one embodiment of the present invention, a gram positive microorganism MP polynucleotide may be ligated to a heterologous sequence to encode a fusion protein. A fusion protein may also be engineered to contain a cleavage site located between the metalloprotease nucleotide sequence and the heterologous protein sequence, so that the metalloprotease may be cleaved and purified away from the heterologous moiety.

IV. Vector Sequences

Expression vectors used in expressing the metalloproteases of the present invention in gram positive microorganisms comprise at least one promoter associated with MP, which promoter is functional in the host cell. In one embodiment of the present invention, the promoter is the wild-type promoter for the selected metalloprotease and in another embodiment of the present invention, the promoter is heterologous to the metalloprotease, but still functional in the host cell. In one preferred embodiment of the present invention, nucleic acid encoding the metalloprotease is stably integrated into the microorganism genome.

In a preferred embodiment, the expression vector contains a multiple cloning site cassette which preferably comprises at least one restriction endonuclease site unique to the vector, to facilitate ease of nucleic acid manipulation. In a preferred embodiment, the vector also comprises one or more selectable markers. As used herein, the term "selectable marker" refers to a gene capable of expression in the gram positive host which allows for ease of selection of those hosts containing the vector. Examples of such selectable markers include but are not limited to antibiotics, such as, erythromycin, actinomycin, chloramphenicol and tetracycline.

V. Transformation

A variety of host cells can be used for the production Bacillus subtilis MP or MP homologues including bacterial, fungal, mammalian and insects cells. General transformation procedures are taught in *Current Protocols In Molecular Biology*, (Vol. 1, edited by Ausubel et al., John Wiley & Sons, Inc., 1987, Chapter 9) and include calcium phosphate methods, transformation using DEAE-Dextran and electroporation. Plant transformation methods are taught in Rodriquez (WO 95/14099, published 26 May 1995).

In a preferred embodiment, the host cell is a gram positive microorganism and in another preferred embodiment, the host cell is *Bacillus*. In one embodiment of the present invention, nucleic acid encoding one or more metalloprotease(s) of the present invention is introduced into a host cell via an expression vector capable of replicating within the *Bacillus* host cell. Suitable replicating plasmids for *Bacillus* are described in *Molecular Biological Methods for Bacillus*, Ed. Harwood and Cutting, John Wiley & Sons, 1990, hereby expressly incorporated by reference; see chapter 3 on plasmids. Suitable replicating plasmids for *B. subtilis* are listed on page 92.

In another embodiment, nucleic acid encoding a metalloprotease(s) of the present invention is stably integrated into the microorganism genome. Preferred host cells are gram positive host cells. Another preferred host is *Bacillus*. Another preferred host is *Bacillus subtilis*. Several strategies have been described in the literature for the direct cloning of DNA in *Bacillus*. Plasmid marker rescue transformation involves the uptake of a donor plasmid by competent cells carrying a partially homologous resident plasmid (Contente et al., *Plasmid*, 2:555–571 (1979); Haima et al., *Mol. Gen. Genet.*, 223:185–191 (1990); Weinrauch et al., *J. Bacteriol.*, 154(3):1077–1087 (1983); and Weinrauch et al., *J. Bacteriol.*,169(3):1205–1211 (1987)). The incoming donor plasmid recombines with the homologous region of the resident "helper" plasmid in a process that mimics chromosomal transformation.

Transformation by protoplast transformation is described for *B. subtilis* in Chang and Cohen, (1979), *Mol. Gen. Genet.*, 168:111–115; for *B. megaterium* in Vorobjeva et al., (1980), *FEMS Microbiol. Letters*, 7:261–263; for *B. amyloliquefaciens* in Smith et al., (1986), *Appl. and Env. Microbiol.*, 51:634; for *B. thuringiensis* in Fisher et al., (1981), *Arch. Microbiol.*, 139:213–217; for *B. sphaericus* in McDonald, (1984), *J. Gen. Microbiol.*, 130:203; and *B. larvae* in Bakhiet et al., (1985, Appl. Environ. Microbiol. 49:577). Mann et al., (1986, *Current Microbiol.*, 13:131–135) report on transformation of *Bacillus* protoplasts and Holubova, (1985), Folia Microbiol., 30:97) disclose methods for introducing DNA into protoplasts using DNA containing liposomes.

VI. Identification of Transformants

Whether a host cell has been transformed with a mutated or a naturally occurring gene encoding a gram positive MP, detection of the presence/absence of marker gene expression can suggest whether the gene of interest is present. However, its expression should be confirmed. For example, if the nucleic acid encoding a metalloprotease is inserted within a marker gene sequence, recombinant cells containing the insert can be identified by the absence of marker gene function. Alternatively, a marker gene can be placed in tandem with nucleic acid encoding the metalloprotease under the control of a single promoter. Expression of the marker gene in response to induction or selection usually indicates expression of the metalloprotease as well.

Alternatively, host cells which contain the coding sequence for a metalloprotease and express the protein may be identified by a variety of procedures known to those of skill in the art. These procedures include, but are not limited to, DNA—DNA or DNA-RNA hybridization and protein bioassay or immunoassay techniques which include membrane-based, solution-based, or chip-based technologies for the detection and/or quantification of the nucleic acid or protein.

The presence of the metalloprotease polynucleotide sequence can be detected by DNA—DNA or DNA-RNA hybridization or amplification using probes, portions or fragments of *B. subtilis* MP.

VII. Assay of Protease Activity

There are various assays known to those of skill in the art for detecting and measuring protease activity. There are assays based upon the release of acid-soluble peptides from casein or hemoglobin measured as absorbance at 280 nm or calorimetrically using the Folin method (Bergmeyer, et al., 1984, *Methods of Enzymatic Analysis*, Vol. 5, Peptidases, Proteinases and their Inhibitors, Verlag Chemie, Weinheim). Other assays involve the solubilization of chromogenic substrates (Ward, 1983, Proteinases, in *Microbial Enzymes and Biotechnology*, (W. M. Fogarty, ed.), Applied Science, London, pp. 251–317).

VIII. Secretion of Recombinant Proteins

Means for determining the levels of secretion of a heterologous or homologous protein in a gram positive host cell and detecting secreted proteins include using either polyclonal or monoclonal antibodies specific for the protein. Examples include enzyme-linked immunosorbent assay (ELISA), radioimmunoassay (RIA) and fluorescent activated cell sorting (FACS). These and other assays are described, among other places, in Hampton, R. et al., (1990, *Serological Methods, a Laboratory Manual*, APS Press, St. Paul Minn.) and Maddox, D E et al., (1983, *J. Exp. Med.*, 158:1211).

A wide variety of labels and conjugation techniques are known by those skilled in the art and can be used in various nucleic and amino acid assays. Means for producing labeled hybridization or PCR probes for detecting specific polynucleotide sequences include oligolabeling, nick translation, end-labeling or PCR amplification using a labeled nucleotide. Alternatively, the nucleotide sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp. (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277, 437; 4,275,149 and 4,366,241. Also, recombinant immunoglobulins may be produced as shown in U.S. Pat. No. 4,816,567 and incorporated herein by reference.

IX. Purification of Proteins

Gram positive host cells transformed with polynucleotide sequences encoding heterologous or homologous protein may be cultured under conditions suitable for the expression and recovery of the encoded protein from cell culture. The protein produced by a recombinant gram positive host cell comprising a mutation or deletion of the metalloprotease activity will be secreted into the culture media. Other recombinant constructions may join the heterologous or homologous polynucleotide sequences to a nucleotide sequence encoding a polypeptide domain which will facilitate purification of soluble proteins (Kroll, DJ. et al., (1993), *DNA Cell Biol.* 12:441–53).

Such purification facilitating domains include, but are not limited to, metal chelating peptides such as histidine-tryptophan modules that allow purification on immobilized metals (Porath, J., (1992), *Protein Expr. Purif.* 3:263–281), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the heterologous protein can be used to facilitate purification.

X. Uses of The Present Invention

MP and Genetically Engineered Host Cells

The present invention provides genetically engineered host cells comprising mutations, preferably non-revertable mutations, or deletions in the naturally occurring gene encoding MP such that the proteolytic activity is diminished or deleted altogether. The host cell may contain additional protease deletions, such as deletions of the mature subtilisn protease and/or mature neutral protease disclosed in U.S. Pat. No. 5,264,366.

In a preferred embodiment, the host cell is further genetically engineered to produce a desired protein or polypeptide. In a preferred embodiment, the host cell is a *Bacillus*. In a further preferred embodiment, the host cell is a *Bacillus subtilis*.

In an alternative embodiment, a host cell is genetically engineered to produce a gram positive MP. In a preferred embodiment, the host cell is grown under large scale fermentation conditions. In another preferred embodiment, the MP is isolated and/or purified and used in the textile industry, the feed industry and in cleaning compositions such as detergents.

As noted, MP can be useful in formulating various cleaning compositions. A number of known compounds are suitable surfactants useful in compositions comprising the MP of the invention. These include nonionic, anionic, cationic, anionic or zwitterionic detergents, as disclosed in U.S. Pat. No. 4,404,128 and U.S. Pat. No. 4,261,868. A suitable detergent formulation is that described in Example 7 of U.S. Pat. No. 5,204,015. The art is familiar with the different formulations which can be used as cleaning compositions. In addition, MP can be used, for example, in bar or liquid soap applications, dishcare formulations, contact lens cleaning solutions or products, peptide hydrolysis, waste treatment, textile applications, as fusion-cleavage enzymes in protein production, etc. MP may comprise enhanced performance in a detergent composition (as compared to another detergent protease). As used herein, enhanced performance in a detergent is defined as increasing cleaning of certain enzyme sensitive stains such as grass or blood, as determined by usual evaluation after a standard wash cycle.

MP can be formulated into known powdered and liquid detergents having pH between 6.5 and 12.0 at levels of about 0.01 to about 5% (preferably 0.1% to 0.5%) by weight. These detergent cleaning compositions can also include other enzymes such as known proteases, mylases, cellulases, lipases or endoglycosidases, as well as builders and stabilizers.

The addition of MP to conventional cleaning compositions does not create any special use limitation. In other words, any temperature and pH suitable for the detergent is also suitable for the present compositions as long as the pH is within the above range, and the temperature is below the described MP's denaturing temperature. In addition, MP can be used in a cleaning composition without detergents, again either alone or in combination with builders and stabilizers.

Proteases can be included in animal feed such as part of animal feed additives as described in, for example, U.S. Pat. No. 5,612,055; U.S. Pat. No. 5,314,692; and U.S. Pat. No. 5,147,642.

One aspect of the invention is a composition for the treatment of a textile that includes MP. The composition can be used to treat for example silk or wool as described in publications such as RD 216,034; EP 134,267; U.S. Pat. No. 4,533,359; and EP 344,259.

MP Polynucleotides

A *B. subtlis* MP polynucleotide, or any part thereof, provides the basis for detecting the presence of gram positive microorganism MP polynucleotide homologues through hybridization techniques and PCR technology.

Accordingly, one aspect of the present invention is to provide for nucleic acid hybridization and PCR probes which can be used to detect polynucleotide sequences, including genomic and cDNA sequences, encoding gram positive MP or portions thereof.

The manner and method of carrying out the present invention may be more fully understood by those of skill in the art by reference to the following examples, which examples are not intended in any manner to limit the scope of the present invention or of the claims directed thereto.

EXAMPLE I

Preparation of a Genomic Library

The following example illustrates the preparation of a *Bacillus* genomic library.

Genomic DNA from *Bacillus* cells is prepared as taught in *Current Protocols In Molecular Biology*, Vol. 1, edited by Ausubel et al., John Wiley & Sons, Inc., 1987, Chapter 2.4.1. Generally, *Bacillus* cells from a saturated liquid culture are lysed and the proteins removed by digestion with proteinase K. Cell wall debris, polysaccharides, and remaining proteins are removed by selective precipitation with CTAB, and high molecular weight genomic DNA is recovered from the resulting supernatant by isopropanol precipitation. If exceptionally clean genomic DNA is desired, an additional step of purifying the *Bacillus* genomic DNA on a cesium chloride gradient is added.

After obtaining purified genomic DNA, the DNA is subjected to Sau3A digestion. Sau3A recognizes the 4 base pair site GATC and generates fragments compatible with several convenient phage lambda and cosmid vectors. The DNA is subjected to partial digestion to increase the chance of obtaining random fragments.

The partially digested *Bacillus* genomic DNA is subjected to size fractionation on a 1% agarose gel prior to cloning into a vector. Alternatively, size fractionation on a sucrose gradient can be used. The genomic DNA obtained from the size fractionation step is purified away from the agarose and ligated into a cloning vector appropriate for use in a host cell and transformed into the host cell.

EXAMPLE II

Detection of Gram Positive Microorganisms

The following example describes the detection of gram positive microorganism MP.

DNA derived from a gram positive microorganism is prepared according to the methods disclosed in *Current Protocols in Molecular Biology*, Chap. 2 or 3. The nucleic acid is subjected to hybridization and/or PCR amplification with a probe or primer derived from MP.

The nucleic acid probe is labeled by combining 50 pmol of the nucleic acid and 250 mCi of [gamma $^{32}$P] adenosine triphosphate (Amersham, Chicago Ill.) and T4 polynucleotide kinase (DuPont NEN®, Boston Mass.). The labeled probe is purified with Sephadex G-25 super fine resin column (Pharmacia). A portion containing $10^7$ counts per minute of each is used in a typical membrane based hybridization analysis of nucleic acid sample of either genomic or cDNA origin.

The DNA sample which has been subjected to restriction endonuclease digestion is fractionated on a 0.7 percent agarose gel and transferred to nylon membranes (Nytran Plus, Schleicher & Schuell, Durham N H). Hybridization is carried out for 16 hours at 40 degrees C. To remove nonspecific signals, blots are sequentially washed at room temperature under increasingly stringent conditions up to 0.1× saline sodium citrate and 0.5% sodium dodecyl sulfate. The blots are exposed to film for several hours, the film developed and hybridization patterns are compared visually to detect polynucleotide homologues of *B. subtilis* MP. The homologues are subjected to confirmatory nucleic acid sequencing. Methods for nucleic acid sequencing are well known in the art. Conventional enzymatic methods employ DNA polymerase Klenow fragment, SEQUENASE®) (US Biochemical Corp, Cleveland, Ohio) or Taq polymerase to extend DNA chains from an oligonucleotide primer annealed to the DNA template of interest.

Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated by reference in their entirety.

The invention claimed is:

1. A genetically engineered *Bacillus subtilis* cell comprising a mutation or deletion in a naturally occurring metalloprotease gene which results in the inactivation of the production of the metalloprotease, wherein said gene prior to inactivation or deletion comprises a nucleic acid sequence encoding a metalloprotease having the amino acid sequence set forth in SEQ ID NO:2.

2. The genetically engineered *Bacillus subtilis* cell of claim 1, wherein said gene encoding a naturally occurring metalloprotease comprises the nucleic acid sequence set forth in SEQ ID NO: 1.

3. The genetically engineered *Bacillus subtilis* cell of claim 1, further comprising a nucleic acid sequence encoding at least one exogenous protein.

4. The genetically engineered *Bacillus subtilis* cell of claim 3, wherein said exogenous protein is selected from the group consisting of hormones, enzymes, growth factors, and cytokines.

5. The genetically engineered *Bacillus subtilis* cell of claim 4, wherein said exogenous protein is an enzyme.

6. The genetically engineered *Bacillus subtilis* cell of claim 5, wherein said enzyme is selected from the group consisting of proteases, amylases, cellulases, endoglycosidases, lipases, isomerases, oxidases, reductases, transferases, and phosphatases.

7. An expression vector comprising a nucleic acid encoding a *Bacillus subtilis* metalloprotease comprising the nucleic acid sequence set forth in SEQ ID NO: 1.

8. A host cell comprising an expression vector set forth in claim 7.

9. An isolated metalloprotease having the amino acid sequence set forth in SEQ ID NO:2.

10. A cleaning composition comprising the metalloprotease according to claim 9.

11. An animal feed comprising the metalloprotease according to in claim 9.

12. A composition for the treatment of a textile comprising a metalloprotease according to claim 9.

* * * * *

```
                        SEQUENCE LISTING

<160> NUMBER OF SEQ ID NOS: 2

<210> SEQ ID NO 1
<211> LENGTH: 1900
<212> TYPE: DNA
<213> ORGANISM: Bacillus subtilis
<220> FEATURE:
<221> NAME/KEY: CDS
<222> LOCATION: (134)...(1774)

<400> SEQUENCE: 1
atcaagtcat ttctttcccg tcatataaac tgctcaaatg aaccgctttt gtcaaacatt      60
tctgtataat agacgagaaa tcagtttatt tttcagtata gaagcatttt tattcatagg    120 agggcggaa tca atg aat tgg cag acg aag gac gaa ttg ctg gca ctt        169
            Met Asn Trp Gln Thr Lys Asp Glu Leu Leu Ala Leu
              1               5                  10 tta act tct ctt gtg caa tac gaa agc atc acc ggt tca aag ggc gag     217
Leu Thr Ser Leu Val Gln Tyr Glu Ser Ile Thr Gly Ser Lys Gly Glu
            15                  20                  25 gta gcg ctt gca gag tat ctt tat ttt att ttg aag gac aag ccc tat    265
Val Ala Leu Ala Glu Tyr Leu Tyr Phe Ile Leu Lys Asp Lys Pro Tyr
        30                  35                  40 ttt caa aag cac cct gat gat gta aca cct cat ccg atg gac gat ggc   313
Phe Gln Lys His Pro Asp Asp Val Thr Pro His Pro Met Asp Asp Gly
 45                  50                  55                  60 aga tct ttt ctt acg gct cta gtc aaa aag aag aat gtc aaa aag aca   361
Arg Ser Phe Leu Thr Ala Leu Val Lys Lys Lys Asn Val Lys Lys Thr
                65                  70                  75 gtc ctt ctg ctg agt cat ttt gat gtc gtt gac ata gaa gat tac ggc   409
Val Leu Leu Leu Ser His Phe Asp Val Val Asp Ile Glu Asp Tyr Gly
            80                  85                  90 gaa ttt aaa cat atg gct tgc aag cct gct gag ctt ttg agc tcc ttt   457
Glu Phe Lys His Met Ala Cys Lys Pro Ala Glu Leu Leu Ser Ser Phe
        95                 100                 105
```

-continued

| | |
|---|---|
| tta gag aaa aaa gag ctg ctc ccg gaa cgt gtg aga aga gat gcc gaa<br>Leu Glu Lys Lys Glu Leu Leu Pro Glu Arg Val Arg Arg Asp Ala Glu<br>110                            115                        120 | 505 |
| agc gga gac tgg ctg ttc gga aga ggg acg atg gat atg aaa gcg ggg<br>Ser Gly Asp Trp Leu Phe Gly Arg Gly Thr Met Asp Met Lys Ala Gly<br>125                            130                        135                        140 | 553 |
| ctt tgt att caa ctg tcg atg ctg gag agg gca atg aac ggg cat ttt<br>Leu Cys Ile Gln Leu Ser Met Leu Glu Arg Ala Met Asn Gly His Phe<br>                        145                        150                        155 | 601 |
| gag ggc aat ctg ctg ttg ata acg gtt ccg gac gag gaa gtg aat tca<br>Glu Gly Asn Leu Leu Leu Ile Thr Val Pro Asp Glu Glu Val Asn Ser<br>                        160                        165                        170 | 649 |
| aga ggc atg att gaa gcg gtt cct gca ttg aag gag atg gag aaa aag<br>Arg Gly Met Ile Glu Ala Val Pro Ala Leu Lys Glu Met Glu Lys Lys<br>                 175                        180                        185 | 697 |
| cat gat atc aca tta acc gct tgc ctg aat gcc gaa ccg atg ttt gaa<br>His Asp Ile Thr Leu Thr Ala Cys Leu Asn Ala Glu Pro Met Phe Glu<br>190                            195                        200 | 745 |
| aaa ttt ccc ggc gat cag cag caa tat ttt tat aca gga agc att ggc<br>Lys Phe Pro Gly Asp Gln Gln Gln Tyr Phe Tyr Thr Gly Ser Ile Gly<br>205                            210                        215                        220 | 793 |
| aag gtg ctt gcg ggt ttt ttc tgc aag ggg att gag aca cat gtt gga<br>Lys Val Leu Ala Gly Phe Phe Cys Lys Gly Ile Glu Thr His Val Gly<br>                        225                        230                        235 | 841 |
| gag ccg ttt tca ggt cta aac gca aat tta atg gta tct gag att aac<br>Glu Pro Phe Ser Gly Leu Asn Ala Asn Leu Met Val Ser Glu Ile Asn<br>               240                        245                        250 | 889 |
| cgt ttg ctt gaa ctg aat gct gat tat tgc gaa aag gtt gat ggc gag<br>Arg Leu Leu Glu Leu Asn Ala Asp Tyr Cys Glu Lys Val Asp Gly Glu<br>                        255                        260                        265 | 937 |
| gtc act ccg ccg ccg gta aac tta atg caa aag gac ttg aaa gag gca<br>Val Thr Pro Pro Pro Val Asn Leu Met Gln Lys Asp Leu Lys Glu Ala<br>270                            275                        280 | 985 |
| tat tca gtc cag aca ccg cat aca gcc gtc aca tta ttt aat gtg ctg<br>Tyr Ser Val Gln Thr Pro His Thr Ala Val Thr Leu Phe Asn Val Leu<br>285                            290                        295                        300 | 1033 |
| tca atg aaa cgc tca gct agt gag ctg cat cag atg ctg ctt aaa aca<br>Ser Met Lys Arg Ser Ala Ser Glu Leu His Gln Met Leu Leu Lys Thr<br>                        305                        310                        315 | 1081 |
| gca gaa cag gcg gcg gag gaa atc atg tcg aac gtt cgg aag aaa aca<br>Ala Glu Gln Ala Ala Glu Glu Ile Met Ser Asn Val Arg Lys Lys Thr<br>                 320                        325                        330 | 1129 |
| cag gat ttt caa caa ttt gag cca ttt cag ccg att gag cgg gac gtc<br>Gln Asp Phe Gln Gln Phe Glu Pro Phe Gln Pro Ile Glu Arg Asp Val<br>                        335                        340                        345 | 1177 |
| act gtt ttg aca ttt gat gag ctg gtc tcg cgt gca aaa aag cgt gcg<br>Thr Val Leu Thr Phe Asp Glu Leu Val Ser Arg Ala Lys Lys Arg Ala<br>350                            355                        360 | 1225 |
| ggg atc tcg gaa aca gag cgg gct cta aat tat gcc ttt gct aac agg<br>Gly Ile Ser Glu Thr Glu Arg Ala Leu Asn Tyr Ala Phe Ala Asn Arg<br>365                            370                        375                        380 | 1273 |
| ggg gag ctt gga gac agg gat ttt tcg acg aaa att gtt tct gag ctt<br>Gly Glu Leu Gly Asp Arg Asp Phe Ser Thr Lys Ile Val Ser Glu Leu<br>                        385                        390                        395 | 1321 |
| gct tcg ctt tgt aag gag gat gcg ccg ctc atc gtt ctg ttt tat agt<br>Ala Ser Leu Cys Lys Glu Asp Ala Pro Leu Ile Val Leu Phe Tyr Ser<br>                 400                        405                        410 | 1369 |
| ccg ccg ctt tat cca gct gtt tct tca aag gat gat caa ttg atc aga<br>Pro Pro Leu Tyr Pro Ala Val Ser Ser Lys Asp Asp Gln Leu Ile Arg<br>               415                        420                        425 | 1417 |

-continued

```
aat aca gca gat cag ata aag cat tat gcg gct gag cga tac ggc att    1465
Asn Thr Ala Asp Gln Ile Lys His Tyr Ala Ala Glu Arg Tyr Gly Ile
    430                 435                 440 gca tta cgg gag gtt cag tac ttc ccc gga ctt tcg gac ttg agt tat    1513
Ala Leu Arg Glu Val Gln Tyr Phe Pro Gly Leu Ser Asp Leu Ser Tyr
445                 450                 455                 460 ctt cag ctg gaa aaa cag gag gtt gat gca tac aca agc aat atg ccg    1561
Leu Gln Leu Glu Lys Gln Glu Val Asp Ala Tyr Thr Ser Asn Met Pro
                465                 470                 475 ctc ttt aac aga ggg tat tca ttg cca agc ggt aaa aat cag gct tta    1609
Leu Phe Asn Arg Gly Tyr Ser Leu Pro Ser Gly Lys Asn Gln Ala Leu
            480                 485                 490 tat gtc cca gtt tta aat gtc ggt ccg gct ggt aaa gac ccg cat aaa    1657
Tyr Val Pro Val Leu Asn Val Gly Pro Ala Gly Lys Asp Pro His Lys
        495                 500                 505 tgg acg gaa aga ttg tat atg cct tat tcc ttt gaa gtg ctt ccc gat    1705
Trp Thr Glu Arg Leu Tyr Met Pro Tyr Ser Phe Glu Val Leu Pro Asp
    510                 515                 520 ttg ctt tca ttt acg atc tcc gcg cta tta aag caa tca gaa tct gcc    1753
Leu Leu Ser Phe Thr Ile Ser Ala Leu Leu Lys Gln Ser Glu Ser Ala
525                 530                 535                 540 ggc cag ctg ctg cgg gaa aaa taaaaacag aaggcactgt gccttctgtt        1804
Gly Gln Leu Leu Arg Glu Lys
                545 tttgtcctta catctaagaa tgtctctcta aggcggcacc ggcaaactgt tctttgattt   1864 ctgcgctccg tttagctgtt cttcaatac agtgaa                              1900

<210> SEQ ID NO 2
<211> LENGTH: 547
<212> TYPE: PRT
<213> ORGANISM: Bacillus subtilis

<400> SEQUENCE: 2

Met Asn Trp Gln Thr Lys Asp Glu Leu Leu Ala Leu Leu Thr Ser Leu
1               5                   10                  15

Val Gln Tyr Glu Ser Ile Thr Gly Ser Lys Gly Glu Val Ala Leu Ala
            20                  25                  30

Glu Tyr Leu Tyr Phe Ile Leu Lys Asp Lys Pro Tyr Phe Gln Lys His
        35                  40                  45

Pro Asp Asp Val Thr Pro His Pro Met Asp Asp Gly Arg Ser Phe Leu
    50                  55                  60

Thr Ala Leu Val Lys Lys Asn Val Lys Thr Val Leu Leu Leu
65                  70                  75                  80

Ser His Phe Asp Val Val Asp Ile Glu Asp Tyr Gly Glu Phe Lys His
                85                  90                  95

Met Ala Cys Lys Pro Ala Glu Leu Leu Ser Ser Phe Leu Glu Lys Lys
            100                 105                 110

Glu Leu Leu Pro Glu Arg Val Arg Arg Asp Ala Glu Ser Gly Asp Trp
        115                 120                 125

Leu Phe Gly Arg Gly Thr Met Asp Met Lys Ala Gly Leu Cys Ile Gln
    130                 135                 140

Leu Ser Met Leu Glu Arg Ala Met Asn Gly His Phe Glu Gly Asn Leu
145                 150                 155                 160

Leu Leu Ile Thr Val Pro Asp Glu Glu Val Asn Ser Arg Gly Met Ile
                165                 170                 175

Glu Ala Val Pro Ala Leu Lys Glu Met Glu Lys Lys His Asp Ile Thr
```

```
                    180             185             190
Leu Thr Ala Cys Leu Asn Ala Glu Pro Met Phe Glu Lys Phe Pro Gly
        195                 200                 205

Asp Gln Gln Gln Tyr Phe Tyr Thr Gly Ser Ile Gly Lys Val Leu Ala
        210                 215                 220

Gly Phe Phe Cys Lys Gly Ile Glu Thr His Val Gly Glu Pro Phe Ser
225                 230                 235                 240

Gly Leu Asn Ala Asn Leu Met Val Ser Glu Ile Asn Arg Leu Leu Glu
                245                 250                 255

Leu Asn Ala Asp Tyr Cys Glu Lys Val Asp Gly Glu Val Thr Pro Pro
                260                 265                 270

Pro Val Asn Leu Met Gln Lys Asp Leu Lys Glu Ala Tyr Ser Val Gln
        275                 280                 285

Thr Pro His Thr Ala Val Thr Leu Phe Asn Val Leu Ser Met Lys Arg
        290                 295                 300

Ser Ala Ser Glu Leu His Gln Met Leu Leu Lys Thr Ala Glu Gln Ala
305                 310                 315                 320

Ala Glu Glu Ile Met Ser Asn Val Arg Lys Lys Thr Gln Asp Phe Gln
                325                 330                 335

Gln Phe Glu Pro Phe Gln Pro Ile Glu Arg Asp Val Thr Val Leu Thr
                340                 345                 350

Phe Asp Glu Leu Val Ser Arg Ala Lys Lys Arg Ala Gly Ile Ser Glu
                355                 360                 365

Thr Glu Arg Ala Leu Asn Tyr Ala Phe Ala Asn Arg Gly Glu Leu Gly
        370                 375                 380

Asp Arg Asp Phe Ser Thr Lys Ile Val Ser Glu Leu Ala Ser Leu Cys
385                 390                 395                 400

Lys Glu Asp Ala Pro Leu Ile Val Leu Phe Tyr Ser Pro Leu Tyr
                405                 410                 415

Pro Ala Val Ser Ser Lys Asp Asp Gln Leu Ile Arg Asn Thr Ala Asp
                420                 425                 430

Gln Ile Lys His Tyr Ala Ala Glu Arg Tyr Gly Ile Ala Leu Arg Glu
        435                 440                 445

Val Gln Tyr Phe Pro Gly Leu Ser Asp Leu Ser Tyr Leu Gln Leu Glu
        450                 455                 460

Lys Gln Glu Val Asp Ala Tyr Thr Ser Asn Met Pro Leu Phe Asn Arg
465                 470                 475                 480

Gly Tyr Ser Leu Pro Ser Gly Lys Asn Gln Ala Leu Tyr Val Pro Val
                485                 490                 495

Leu Asn Val Gly Pro Ala Gly Lys Asp Pro His Lys Trp Thr Glu Arg
                500                 505                 510

Leu Tyr Met Pro Tyr Ser Phe Glu Val Leu Pro Asp Leu Leu Ser Phe
        515                 520                 525

Thr Ile Ser Ala Leu Leu Lys Gln Ser Glu Ser Ala Gly Gln Leu Leu
        530                 535                 540

Arg Glu Lys
545
```